(12) United States Patent
Weber et al.

(10) Patent No.: US 6,341,831 B1
(45) Date of Patent: Jan. 29, 2002

(54) SKIN DECORATION APPARATUS AND METHOD

(76) Inventors: Paul J. Weber, 1 Seneca Rd., Ft. Lauderdale, FL (US) 33308; Luiz B. Da Silva, 1995 Camino Ramon Pl., Danville, CA (US) 94526; Michael R. Weber, 13906 Tern La., Clearwater, FL (US) 33762

( * ) Notice: Subject to any disclaimer, the term of this patent is extended or adjusted under 35 U.S.C. 154(b) by 0 days.

(21) Appl. No.: 09/475,641

(22) Filed: Dec. 30, 1999

Related U.S. Application Data

(63) Continuation-in-part of application No. 09/264,778, filed on Mar. 9, 1999.

(51) Int. Cl.[7] .............................. B41J 2/005; B41J 2/01
(52) U.S. Cl. ............................................. 347/1; 347/2
(58) Field of Search .................... 347/2, 1, 85; 118/300, 118/313

(56) References Cited

U.S. PATENT DOCUMENTS

| | | | | |
|---|---|---|---|---|
| 4,764,780 A | * | 8/1988 | Yamamori | 137/625.12 |
| 5,757,389 A | * | 5/1998 | Schwede et al. | 347/4 |
| 5,944,893 A | * | 8/1999 | Anderson | 118/300 |
| 5,958,560 A | * | 9/1999 | Ewan | 428/201 |
| 5,972,111 A | * | 10/1999 | Anderson | 118/300 |
| 6,042,881 A | * | 3/2000 | Ewan | 347/105 |

* cited by examiner

Primary Examiner—Huan Tran
(74) Attorney, Agent, or Firm—L. E. Carnahan

(57) ABSTRACT

The human body is decorated with highly detailed, multicolored, personalized designs using Wirejet™ or electronically controlled ink ejection or similar printing technology. The designs are applied to the epidermal and upper dermal skin layers and last for at least several weeks. The decoration is produced by a print head comprising Wirejet™ nozzles, which spray biocompatible inks or dyes onto the skin. The Wirejet™ may be connected to a scanning mechanism to scan in one, two, or three directions. The decorations can be applied to contoured skin surfaces following flattening against a screen of intersecting wires, by robotic arm, or using z-axis technology. A computer stores the desired design and controls the firing of the Wirejet™ to produce the desired decoration or tattoo.

22 Claims, 4 Drawing Sheets

SKIN DECORATION APPARATUS AND METHOD

This application is a continuation-in-part of U.S. patent application Ser. No. 09/264,778, filed Mar. 9, 1999.

BACKGROUND OF THE INVENTION

1. Field of the Invention

The present invention relates to digital decorating or tattooing of living skin using Wirejet™ or similar printing technology. The present invention also relates to digitally decorating adnexal structures of living skin such as hair or nails using Wirejet™ or similar printing technology.

2. Description of Related Art

Decorating the human skin by applying colored inks or dyes to produce temporary decorations or permanent tattoos has a long history. Tattooing by puncturing the skin with a sharp tool or needle to introduce a dye under the uppermost layer of skin was practiced by the Egyptians. The inks used in tattoos are composed of organic and inorganic pigments of varying colors with particles typically larger than 10–50 microns in diameter. The large particle size prevents the particles from being engulfed by the macrophages that reside in the dermis.

To produce a permanent tattoo, these dyes or inks must be injected into the dermis with needles, which limits the degree of detail and leads to irregular penetration depths. This method of tattooing can be painful and possibly dangerous if the needles have not been properly sterilized. In addition, permanent tattoos are undesirable because the wearer often reconsiders after a period of time and then must undergo a removal procedure, which is often expensive, painful, and not 100% effective. Even current laser tattoo removal technology cannot uniformly destroy the pigment and remove the coloration from the skin because of the varying penetration depths of the dyes.

Washable or "rub-on" tattoos are commercially available which can be easily applied to the epidermis. These decorations are temporary and wear off or wash off with time, typically lasting only a week. Just as in newspapers and newsprint, with "press-on or rub-on" tattoos increasing the number of colors increases the cost, therefore, color multiplicity and availability are extremely limited. Additionally, although these tattoos afford the advantage of being temporary and easily removable, the available designs or images are also limited and not personalized.

Thus, it would be advantageous to provide a digital method for decorating the skin with custom-made, highly detailed, designs. Such designs could provide a more detailed, artful, colorful and "fresher" look than "press-on" tattoos that are limited in colors and may look like a "sheet". Furthermore, it would be beneficial for the device to apply such skin decorations easily, economically, and quickly, without pain or the risk of injury.

Some inkjets use thermal technology, whereby heat is used to fire ink onto a substrate. There are three main stages with this method. The squirt is initiated by heating the ink to create a bubble until the pressure forces it to burst and hit the paper. The bubble then collapses as the element cools, and the resulting vacuum draws ink from the reservoir to replace the ink that was ejected.

Tiny heating elements are used to eject ink droplets from the print-bead's nozzles, thermal inkjets have print heads containing between 300 and 600 nozzles in total, each about the diameter of a human hair (approx. 70 microns). These deliver drop volumes of around 8–10 picolitres (a picolitre is a million millionth of a liter), and dot sizes of between 50 and 60 microns in diameter. By comparison, the smallest dot size visible to the naked eye is around 30 microns. Dye-based cyan, magenta and yellow inks are normally delivered via a combined CMY print-head. Several small color ink drops—typically between four and eight—can be combined to deliver a variable dot size, a bigger palette of non-halftones colors and smoother halftones. Black ink, which is generally based on bigger pigment molecules, is delivered from a separate print-head in larger drop volumes of around 35 pt. Nozzle density, corresponding to the printer native resolution varies between 300 and 600 dpi, with enhanced resolution of 1200 dpi increasingly available. Print speed is chiefly a function of the frequency with which the nozzles can be made to fire ink drops and the width of the swath printed by the print-head. Typically this is around 12 MHz and half an inch respectively.

Another variant of inkjet, the piezoelectric inkier, uses a piezo crystal at the back of the ink reservoir similar to a loudspeaker cone—flexing when an electric current flows through it. So, whenever a dot is required, a current is applied to the piezo element, the element flexes and in so doing forces a drop of ink out of the nozzle.

There are several advantages to the piezo method. The process allows more control over the shape and size of ink droplet release. The tiny fluctuations in the crystal allow for smaller droplet sizes and hence higher nozzle density. Also, unlike with thermal technology, the ink does not have to be heated and cooled between each cycle. This saves time, and the ink itself is tailored more for its absorption properties than its ability to withstand high temperatures. This allows more freedom for developing new chemical properties in inks.

Although there are many benefits such as the possibility to now deposit 1600 dpi, there are also disadvantages to using inkjets to decorate the body. First and foremost are cost and availability of the highly purified and specialized inks or dyes that are able to pass through the inkjet heads or other device passageways. Small particles or impurities in imperfect inks or dyes could cause inkjet head failure. Viscosity, solvent mixture and density must also be precise to avoid failure. Thus it would be advantageous to have a computer-controlled system that is more tolerant to ink or dye composition that is less prone to clogging or print head failure.

Thus it would be beneficial to provide a means for decorating the skin or adnexal structures of an animal or human body using a technology that is digital, relatively rapid, and able to apply a wide range of inexpensive dyes, inks or liquid pigments without the possibility of mechanical failure due to particle size, thermal characteristics, filter clogging, solvent mix composition and ratios or impurity presence. The use of Wirejet™ technology obviates these particular problems. A drawback of the Wirejet™ technology when compared with the newer inkjet technology is that the Wirejet™ is purported to have a limited maximum of 500 dpi resolution as opposed to newer inkjets with 1600 dpi and increasing annually.

Wirejet™ technology has been described in U.S. Pat. Nos. 5,944,893 and 5,972,111 to Anderson. The Wirejet™ is in essence a wire "conveyor belt" that is externally coated with a liquid pigmented medium via surface tension and adherence upon passing through a given liquid pigment reservoir. The externally coated wire (cable, line, string, cord, etc) then passes in front of a compressed air nozzle whereupon the ink is controllably carried by air (or another gas) to the target medium. In the abstract, Anderson describes the Wirejet™ as a paint injector for digital printing. In Anderson, wheels carry the wire through the paint reservoir whereupon the wire is coated. The wire is further drawn controllably by computer in front of the air stream that pulls the ink or paint from the wire and carries it toward the print medium. By employing a plurality of paint injectors, each with a different color of paint a digital image can be painted by the print head on the print medium. As in inkjet printing, the use of the C,M,Y,K color scheme with white can provide for virtually limitless color combinations.

Wirejet™ technology differs from airbrush technology in which a short, rigid, needle or pin is externally coated with paint or liquid pigment that is then carried onto the target medium by pressurized air from a nozzle.

Another type of print head system differs from the Wirejet™ and is disclosed in U.S. Pat. No. 4,764,780 to Yamamori et al; and may be considered by some to be a variant of an inkjet system. Yamamori is a system designed for inking a recording medium using a plurality of electrically-controlled ink ejection heads connected to a reservoir. As ink is presented by the ejection heads a pressurized air stream is directed by nozzle to carry the ink droplets onto the recording medium. A key difference between the devices of Yamamori and Anderson is that ink is carried internally to the air-stream by Yamamori, while in Anderson the pigmented substance (ink, dye, etc.) is carried from the reservoir to the air-stream externally on wires (or the outer surfaces of lines, cables, strings or cords).

The present invention provides a method for decorating the skin with custom-made, highly detailed, temporary designs. Furthermore, it would be beneficial for the device to apply such skin decorations easily, economically, and quickly, without pain or the risk of injury. The present invention provides a simple and economical process for decorating human skin.

SUMMARY OF THE INVENTION

The present invention is a method and apparatus for decorating the human body using Wirejet™ or similar printing technology. An objective of the invention is to print multicolored images on human skin or appendageal products using biocompatible inks or dyes. The decoration is produced by a print head comprising an array of Wirejet™ or other electronically controlled ink ejection nozzles, which can be connected to a scanning mechanism. The print head may be scanned in one, two, or three directions to cover the area of the body to be decorated. Highly contoured anatomic surfaces such as the shoulders, breasts and buttocks may be "flattened" by compression against intersecting restraining wires for proper Wirejet™ application of tattoo inks or dyes. A computer stores the desired design and controls the firing of the apparatus to produce designs on the skin.

In another embodiment, a housing is connected to wheels that are encoded and roll over the skin surface, and a computer synchronizes the firing of the print head nozzles as the housing is moved over the skin. Further enhancement of z-axis capabilities of the current Wirejet™ are herein described that enable the device to better handle the extreme curvatures of the living human or animal body as opposed to the relatively flat or predictably planar and angled print or non-living media that is the current target for Wirejet™ technology.

The described use of the Wirejet™ provides for the opportunity to decorate body surfaces with detailed, temporary personalized designs. If the surface layer of dead skin cells is removed, prior to Wirejet™ tattoo dye or ink application, the decoration will then be applied to the epidermis or upper dermis, and the design will last until those skin layers are sloughed off, which typically takes about a month. These decorations or tattoos, therefore, will last longer than the currently available temporary decal-type tattoos that are transferred to the surface of the skin by rubbing.

Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

The following examples and accompanying drawings, which are incorporated into and form part of this disclosure, illustrate embodiments of the invention and together with the description, serve to explain the principles of the invention.

Figure 1:
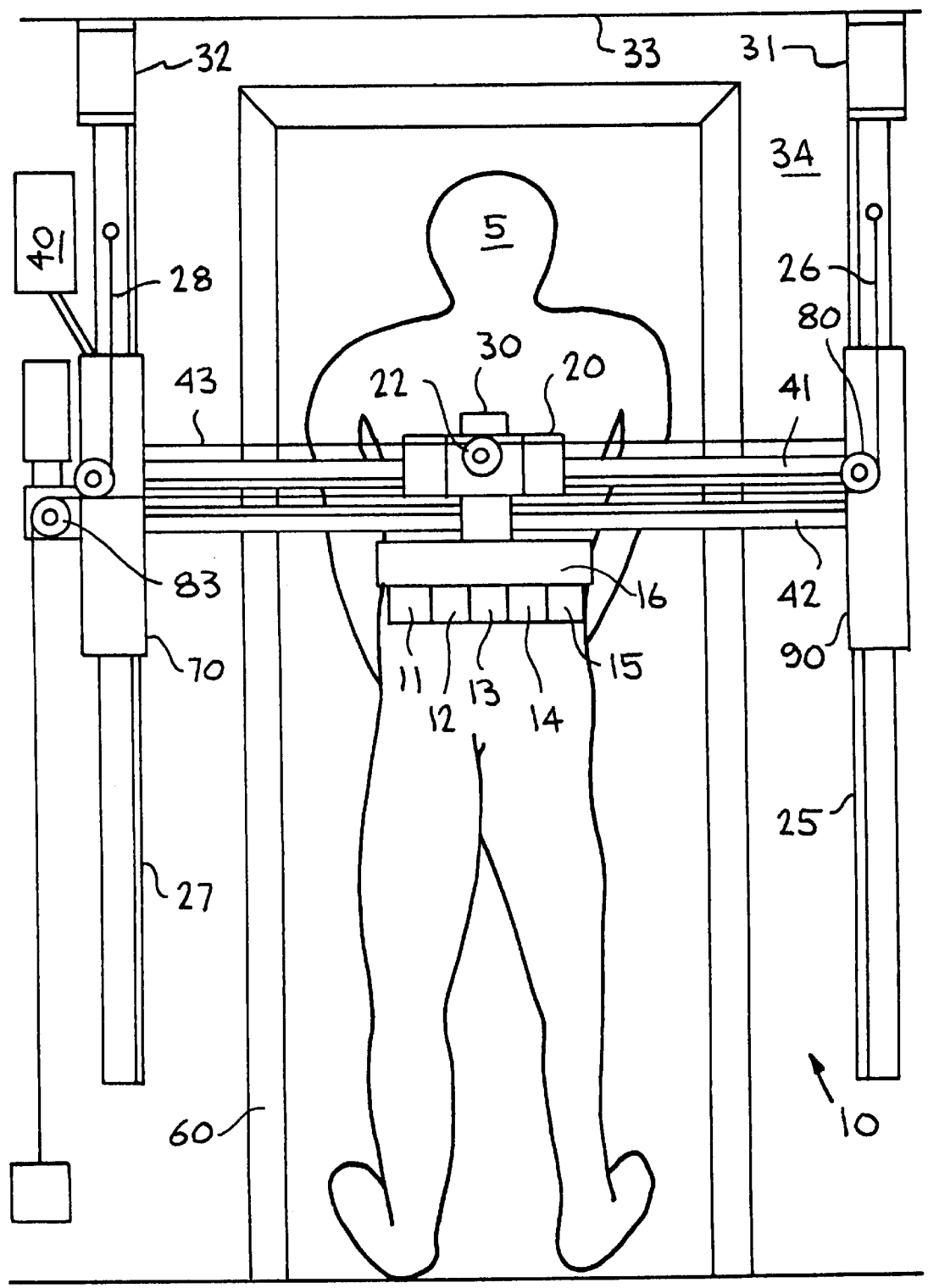
FIG. 1 Shows present invention (skin decoration apparatus) in use.

FIG. 1 shows an embodiment of a device according to the present invention that enables carrying out the method of the invention. FIG. 1 shows the skin-decorating apparatus 10 of the present invention as it is being used on a living human 5 as human stands in a doorway or break 60 in a wall 34 near support ceiling 33. Apparatus 10 is powered by motor 40. Left and right bracket assemblies 32 and 31 are fixed into support ceiling 33. Carriage 20 bearing paint injectors 11,12,13,14 and 15 rides along shafts 41 and 42 and is moved by drive chain 43 and engaged by sprocket 22. Left and right support assemblies 70 and 90 are positioned by or moved along tracks 25 and 27 and z-roller chains 26 and 28. Z-drive sprockets 80 and worm screw 83 influence z-axis movement within the limits of the capabilities of the previous art. Camera with digital output and optical sensors 30 interacts with central processing unit to more finely coordinate x,y,z axis motion.

Figure 2:
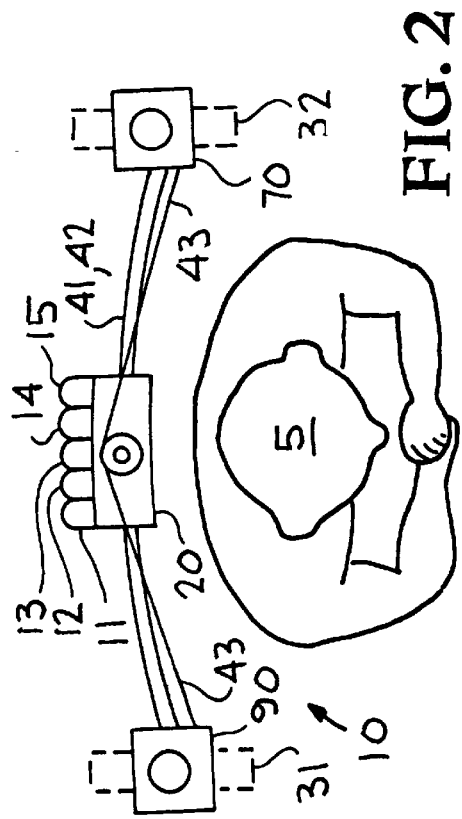
FIG. 2 Shows a top view of skin decoration apparatus with curved ???.

FIG. 2 shows a top view of skin decoration apparatus with carriage 20 moving curved shafts 41 and 42 attached to left and right support assemblies 70 and 90 as apparatus 10 decorates living human subject 5 with pigments from paint injectors 11,12,13,14 and 15. Drive chain 43 becomes taught and linear if chain is made of flexible material in contrast to relatively rigid drive shafts. Left and right bracket assemblies 32 and 31 (dashed areas) are fixed into support ceiling.

Figure 3:
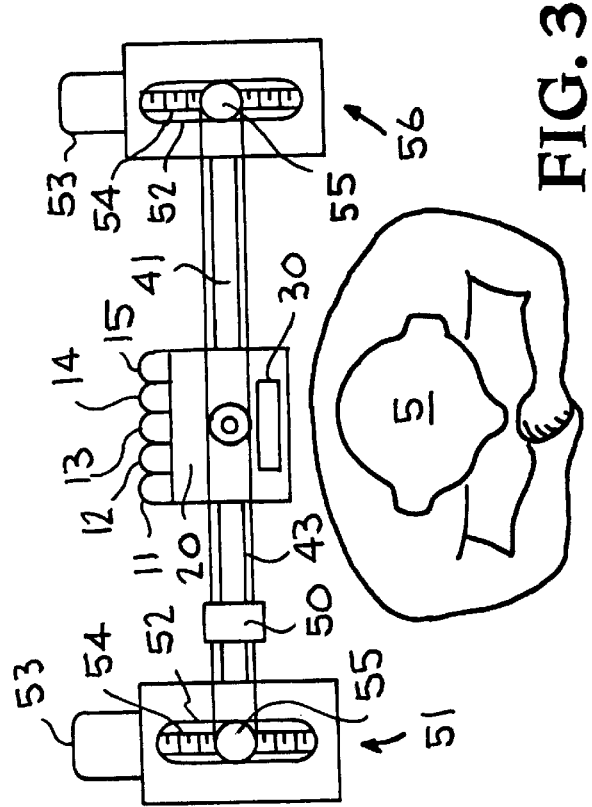
FIG. 3 Shows top view of skin decoration apparatus and ceiling-mounted screw-driven z-axis modifier with camera.

FIG. 3 shows top view of skin decoration apparatus with digital camera or optical sensor 30 and ceiling-mounted screw-driven z-axis modifier. Further enhancement of z-axis capabilities of the current Wirejet™ enable the device to better handle the extreme curvatures of the living human or animal body as opposed to the relatively flat or predictably planar and angled print or non-living media that is the current appreciated target for Wirejet™ technology. Left and right Z-axis enhancers 56 and 51 are mounted on their superior aspects to support ceiling. Left and right Z-axis enhancers 56 and 51 are fixed to left and right bracket assemblies on the inferior aspects of the enhancers. Motors 53 control screws 54 resting in slots 52 of the housing of left and right enhnacers 56 and 51. Screws 54 position short shafts 55 that protrude superiorly from slots 52. Short shafts 55 terminate on movable plate (unseen in this view) capable of sliding along bottom of 51 to which are attached the previously described left and right bracket assemblies. Shaft 41 and accompanying drive chain 43 (shown at edge view) continue to influence movement of carriage 20 and accompanying paint injectors 11,12,13,14, and 15 as they decorate living human subject 5 with pigments. However, sleeve mechanism 50 is present and capable of sliding on portions of 43, sectioned, allows 43 to lengthen and compress based upon forces created by the z-axis modifiers 51 and 56 when in extreme opposing positions (for example left forward and right retracted.

Figure 4:
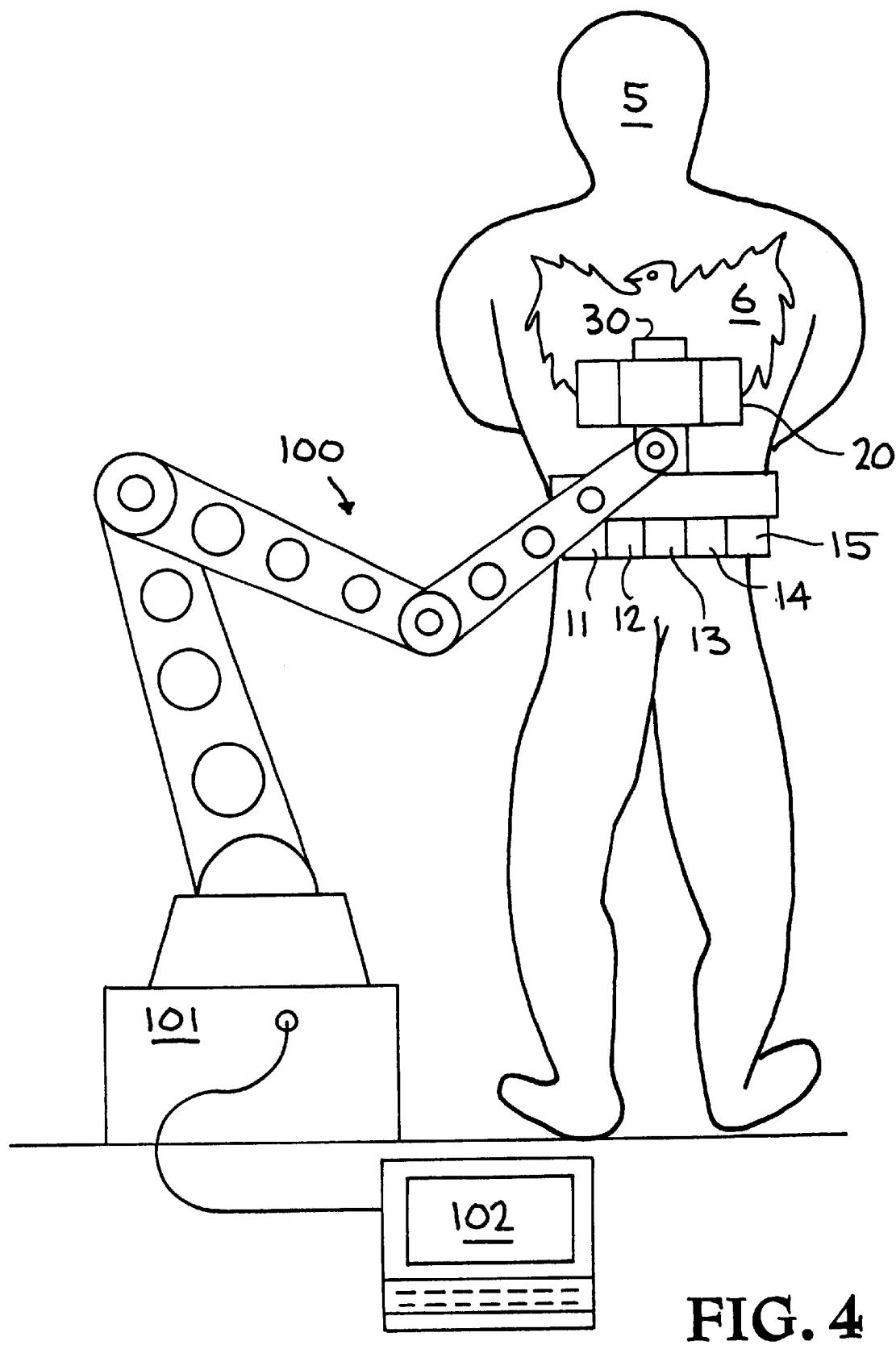
FIG. 4 Shows present invention mounted on robotic arm.

FIG. 4 shows skin decoration apparatus with digital camera or optical sensor 30 mounted on robotic arm 100 sitting on base 101 controlled by feedback from central processing unit of computer 102 and camera/sensor 30. Further enhancement of z-axis capabilities of the current Wirejet™ enable the device to better handle the extreme curvatures of the living human or animal body 5 as opposed to the relatively flat or predictably planar and angled print or non-living media that is the current appreciated target for Wirejet™ technology. Robotic arm 5 with joints and computer control moves carriage 20 and accompanying paint injectors 11,12,13,14, and 15 as they decorate living human subject 5 with pigments creating the artful image 6.

Figure 5:
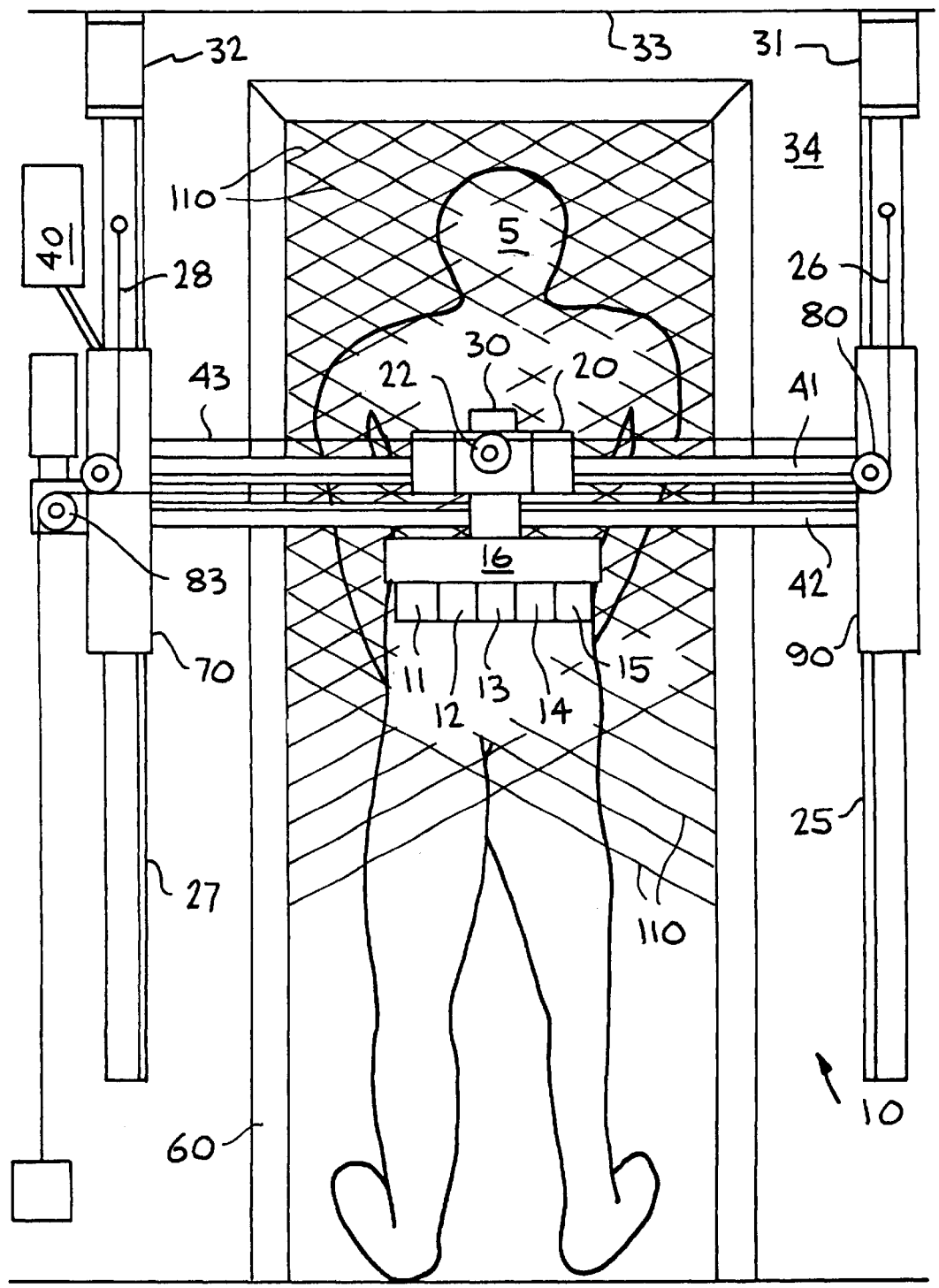
FIG. 5 Shows present invention (skin decoration apparatus) in use with subject and target body decoration zone flattened by pressing against a planar array of restraining wires.

FIG. 5 shows present invention (skin decoration apparatus) in use with subject and target body decoration zone flattened by pressing against a planar array of restraining wires. Standard Wirejet® Unit 10 is located over doorspace 60 with intersecting restraining wire 110 pressing on shoulder or scapula. To enhance of the capabilities of the current Wirejet™ for the extreme curvatures of the living human or animal body (as opposed to the relatively flat or predictably planar and angled print or non-living media that is the current target for Wirejet™ technology) the arced surfaces to be decorated may be compressed against a planar grid or array of intersecting wires 110. Intersecting wires 110 mounted around doorway or break 60 in a wall 34 near support ceiling 33. Apparatus 10 is powered by motor 40. Left and right bracket assemblies 32 and 31 are fixed into support ceiling 33. Carriage 20 bearing paint injectors 11,12,13,14 and 15 rides along shafts 41 and 42 and is moved by drive chain 43 and engaged by sprocket 22. Left and right support assemblies 70 and 90 are positioned by or moved along tracks 25 and 27 and z-roller chains 26 and 28. Z-drive sprockets 80 and worm screw 83 influence z-axis movement, within the limits of the capabilities of the previous art, as human subject recipient 5 of the art is decorated. The capabilities of the previous art when used in the fashion of FIG. 5 will require an artist with brush or other painting instrument to, by hand, fill-in the areas of skin or skin appendage that were occluded by the restraining wires 110.

Figure 6:
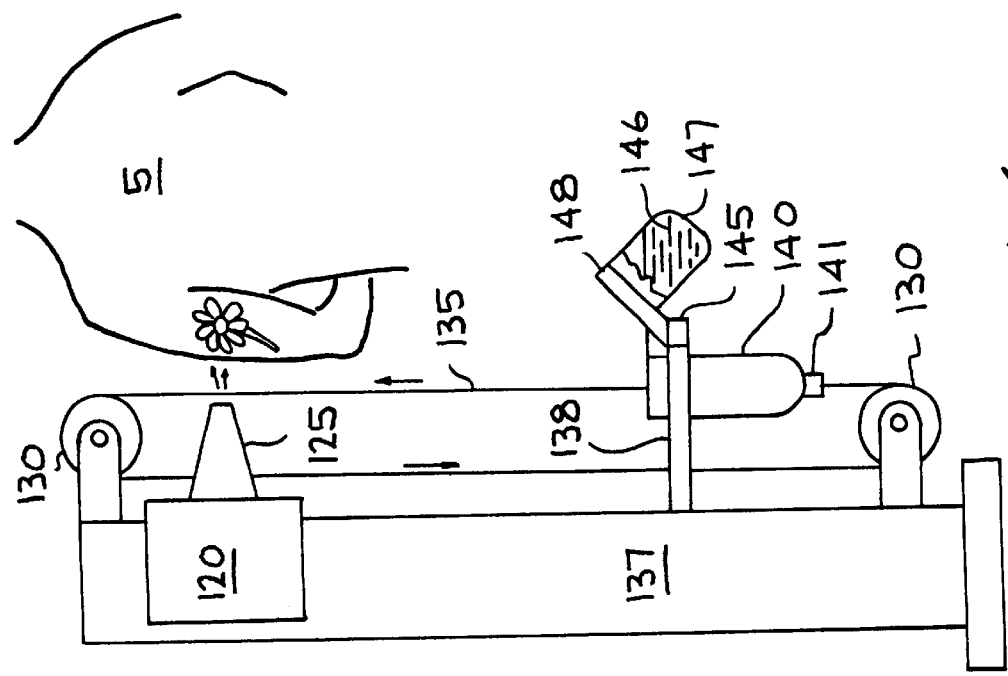
FIG. 6 Shows pigment sparing tube-coating modification of present invention in close-up view.

FIG. 6 shows pigment sparing tube-coating modification of present invention in close-up view. Modification of current art of Wirejet™ is necessary using smaller reservoirs to reduce ink wastage and usage. Nozzle body 120 ejects compressed air through nozzle 125 onto wire 135 containing pigments removed from miniaturized pigment reservoir 140 having a limited seal 141 at its base or in an invaginating seal rising vertically inside from the base. Pigment vial 147 containing a tilted fluid level of liquid pigment 146 is held by clamp arm 145 to the miniaturized pigment reservoir 140 and is secured by collar 148. Support structures 137 and 138 maintain the relationship of the elements between which pass wire 135 on superior and inferior wheels numbered 130 to deposit pigmented skin decoration on human subject 5.

The foregoing description of preferred embodiments of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

FURTHER DETAILED DESCRIPTION OF THE INVENTION

Scanning in two directions that are substantially parallel to the skin surface is sufficient for areas that are fairly flat, such as on the chest or back. Scanning in three directions allows the apparatus to print with high resolution on a highly contoured surface such as an arm, an ankle, or a breast.

The print head has an array of nozzles, where the array can be of any size, depending on various factors, including the surface area to be decorated, and the printing speed and level of complexity desired. For example, the print head could contain as few as three nozzles, to deliver three primary colors, or the array could include more nozzles.

The ink should be non-toxic, biocompatible, and preferably of vegetable or mineral origin, where either organic or inorganic compounds can be used. Examples of such inks include the green, black, red, blue, yellow Amunez Tattoo Paints, Amunez International, Australia and Indonesia. Fluorescent inks or other luminescent compounds could be used to apply "glow in the dark" tattoos. Water-soluble inks could be used for making test decorations, which could be evaluated and easily washed off. Modification using smaller reservoirs and tubular coating devices may be beneficially reduce ink cost and usage. If a prospective permanent tattoo client finds the temporary 3 week version of the tattoo satisfactory, then the permanent version using or permanent tattoo colors could be traditionally using the temporary version as a guide. Liposome technology could be used to encapsulate the inks or dyes so that deeper skin penetration is possible thus lengthening the life of the decoration beyond three weeks. Inks used in the present invention may be pre-sterilized or contain preservatives so that germs or bacteria do not grow in them, which could cause serious skin infections. Alternatively, antibiotics could be mixed with the inks. The inks may be rapid-drying (in a volatile solvent), or may require slight heating (e.g., under a heat lamp or heat blower or other method to "set" the design). Inks that set with exposure to various other electromagnetic spectral wavelengths (e.g., ultraviolet) may be used to "set" the design as well.

After the apparatus is placed next to the surface of the skin in preparation for printing an image, a computer electronically controls (e.g., through cable) the translation of the print head and firing of the nozzles to generate the selected decoration. The computer controls the position and firing of the Wirejet™ with multiple colored inks, thus allowing a multicolored image or pattern to be placed on any part of the human body. The subject-user can select any image that can be stored in the computer, including simple patterns, artwork, graphics, or scanned pictures. Personalized images could be scanned to produce a digital file. Using methods known in the art, these digital images are processed to control the scanning and firing of the Wirejet™ nozzle to produce the desired skin decoration.

The image can be of various sizes depending on the parts of the body to be decorated and the image sizes to be produced. For example, a 10 to 100 cm$^2$ image can be used to decorate small areas such as hands, shoulders, or feet. Large designs may be applied in a mosaic fashion, where scanning is performed over a given area to apply a portion of the design, then moved to the adjacent area to apply the next portion. The various portions of the designs may be aligned by optical means or simply by visual inspection using reference marks on the apparatus and skin.

The size of the area to be decorated can be determined by simple physical measurements or by using a calibrated electronic camera and computer system. An electronic camera system could also be used to determine the topography of the surface to be printed. For example, the camera system can use grid projection or moiré techniques known in the art to map the surface topography. The topography data can be used to control the distance between the print head and the skin surface.

In all embodiments, a sensor may be used to measure the separation or distance of the nozzles from the skin surface. This distance is normal to the skin surface or in the vertical or Z direction. The sensor can be a mechanical probe that lightly touches the skin or an optical sensor where the signal amplitude is proportional to the separation. The sensor signal can be used as a feedback control to maintain a constant nozzle to skin separation and thereby improve image quality. A simple spacer or spacers may be used to maintain a substantially constant physical distance between nozzles and the skin surface.

Before the decoration is applied, the skin can be prepared by cleaning the skin using an appropriate cleaner (e.g., alcohol, acetone) and an abrasive cloth (gauze, buff-puffs, abrasive wash sponge). Vigorous rubbing will remove excessive dead surface skin cells, which improves ink penetration into the skin and may extend the lifetime of the decoration. On most areas of the body, skin cells migrate in the epidermis from the deep basal layer through the prickle cell layer and into the granular layer. These cells eventually become the dead surface layers. The process of cell transit from the bottommost cells to the top surface of the skin usually takes about thirty days. Ink or dye application in the epidermal layers, therefore, leads to a temporary decoration that lasts at most 30 days. Examples of such inks include the green, black, red, blue, yellow Amunez Tattoo Paints, Amunez International, Australia and Indonesia.

Aside from the superficial process of applying ink to the epidermis, there may be a deeper and longer-lasting form of inkjet tattooing that could take place if the epidermis was removed by an instrument such as a laser, or by salabrasion (salt-abraded) or dermabrasion. Epidermal removal would expose the collagen or dermal layers, which would provide easier access the upper dermis where dyes or ink or even biocompatible paints could be permanently applied to the skin. Alternatively, increasing the air pressure driving the Wirejet™ application can be used to shoot the ink through the epidermis to penetrate the dermis.

The foregoing description of preferred embodiments of the invention is presented for purposes of illustration and description and is not intended to be exhaustive or to limit the invention to the precise form disclosed. Many modifications and variations are possible in light of the above teaching.

What is claimed is:

1. An apparatus for decorating at least a curved area of a skin surface with a desired design, comprising:
    an array of Wirejet™ or electronically controlled ink ejection nozzles that deliver biocompatible inks to the skin;
    a scanning means; and
    a control system that stores the desired design and fires the nozzles so as to produce the design on the curved area of the skin.

2. The apparatus as recited in claim 1, wherein the scanning means scans the array in at least two directions.

3. The apparatus as recited in claim 1, wherein the scanning means scan the array in at least three directions.

4. The apparatus as recited in claim 1, further comprising a sensor that detects the distance between the skin surface and the nozzles during delivery of the inks on the skin.

5. The apparatus as recited in claim 1, wherein the array of nozzles is spring-loaded such that the distance is substantially constant during production of the design on the skin.

6. The apparatus as recited in claim 1, further comprising means for maintaining a substantially constant distance between the curved area of the skin surface and the nozzles during production of the design on the skin.

7. An apparatus for decorating contoured area of a skin surface or skin adnexal structure with a desired design, comprising:
    an array of Wirejet™ or electronically controlled ink ejection nozzles that deliver biocompatible inks to the contoured area of the skin;
    a scanning means; and
    a control system that stores the desired design and fires the nozzles so as to produce the design on the contoured area of the skin.

8. The apparatus of claim 7, wherein said scanning means comprising robotic arm.

9. A method for decorating a contoured area of a skin surface with a desired design, comprising:
    storing the desired design in an electronic control system;
    placing a Wirejet™ or electronically controlled ink ejection apparatus over the area of skin to be decorated, wherein a nozzle connected to a control system is capable of delivering biocompatible inks to the contoured area of the skin; and
    controlling the firing of the nozzles so as to produce the desired design on the contoured area of the skin using the control system.

10. The method as recited in claim 9, further comprising scanning the array over the skin in at least one direction.

11. The method as recited in claim 9, further comprising scanning the array over the skin in at least two directions.

12. The method as recited in claim 9, further comprising scanning the array over the skin in at least one direction substantially parallel to the skin surface.

13. The method as recited in claim 9, further comprising scanning the array over the skin in at least one direction substantially normal to the skin surface.

14. The method as recited in claim 9, further comprising scanning the array over the skin in at least three directions.

15. The method as recited in claim 9, further comprising maintaining a substantially constant distance between at least the contoured area of the skin surface and the nozzles during the firing of the nozzles.

16. The method as recited in claim 9, further comprising cleaning and removing surface skin cells from the area to be decorated.

17. The method as recited in claim 9, further comprising removing the epidermis from the area to be decorated.

18. The method as recited in claim 9 for decorating the skin or adnexal structures of an animal or human body using a technology that is digital, relatively rapid, without pain or risk of injury.

19. The method of claim 18, wherein the technology is selected from the group consisting of Wirejet™, electronically controlled ink ejection, Moire technique, and Z-axis scanning.

20. An apparatus that coats the wire of the wirejet with pigment in small amounts including a silicon tube reservoir, and a wire passage seal at base of the reservoir through which the wire passes.

21. The apparatus of claim 1, additionally including a plurality of curved shafts attached to a pair of support assemblies, said array of ink injection nozzles being operatively mounted to said curved shafts.

22. The apparatus of claim 21, additionally including a drive chain operatively mounted to said support assemblies.

* * * * *